United States Patent [19]

Prokai

[11] 4,059,581
[45] Nov. 22, 1977

[54] HETEROCYCLIC NITROGEN CONTAINING SILOXANES

[75] Inventor: Bela Prokai, Mahopac, N.Y.

[73] Assignee: Union Carbide Corporation, New York, N.Y.

[21] Appl. No.: 578,091

[22] Filed: May 16, 1975

Related U.S. Application Data

[60] Continuation-in-part of Ser. No. 219,120, Jan. 19, 1972, abandoned, which is a division of Ser. No. 887,428, Dec. 22, 1969, Pat. No. 3,658,867.

[51] Int. Cl.$^2$ .............................................. C07F 7/04
[52] U.S. Cl. ........................... 544/69; 260/2.5 BB; 260/2.5 AJ; 260/46.5 E; 260/268 R; 260/293.72; 260/293.83; 260/293.84; 260/293.9; 260/326.5 A; 260/326.61; 252/3
[58] Field of Search ............ 260/247, 247.1 L, 268 R, 260/326.5 A, 293.9, 293.83, 293.84, 326.61, 293.72, 247.1 E

[56] References Cited

U.S. PATENT DOCUMENTS

| | | | |
|---|---|---|---|
| 3,402,191 | 9/1968 | Morehouse | 260/448.2 |
| 3,541,127 | 11/1970 | Beattie et al. | 260/247 |
| 3,658,867 | 4/1972 | Prokai | 260/247 |
| 3,769,309 | 10/1973 | Weldes | 260/247 |

*Primary Examiner*—Henry R. Jiles
*Assistant Examiner*—R. W. Ramsuer
*Attorney, Agent, or Firm*—Reynold J. Finnegan

[57] ABSTRACT

Cationic bis(trimethylsiloxy) siloxanes of the formula:

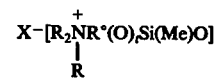

wherein M is the trimethylsiloxy units, $Me_3SiO_{1/2}$, x is an integer of 1 to 3, preferably 1, and D′ is a cationic difunctional siloxy unit of the formula:

$$X^-[R_2\overset{+}{N}R°(O)_tSi(Me)O]$$
$$\underset{R}{|}$$

wherein R° is a divalent organic group, t is 0 to 1, R is methyl or ethyl, $R_2N$ is a five to six member organic heterocyclic ring and X is an anion.

Also the tertiary amino bis(trimethylsiloxy) siloxanes of the formula $MD_xM$ wherein M and x are as defined above and D is a tertiary amino difunctional siloxy unit of the formula:

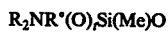

wherein $R_2N$, R° and t are as defined above, which are used in preparing the above cationic siloxanes.

The above cationic siloxanes are useful as emulsifiers, e.g., for water-poly(dimethylsiloxane) oil systems, bacteriocides, antistatic agents, wetting agents and mold release agents.

20 Claims, No Drawings

HETEROCYCLIC NITROGEN CONTAINING SILOXANES

This application is a continuation-in-part of U.S. application Ser. No. 219,120 filed Jan. 19, 1972, now abandoned which in turn is a divisional of U.S. application Ser. No. 887,428 filed Dec. 22, 1969, now U.S. Pat. No. 3,658,867.

This invention relates to novel organosilicon compounds, and, more particularly, to novel low molecular weight siloxanes containing quaternary nitrogen-containing groups or tertiary amine organo groups bonded to carbon.

High molecular weight siloxanes containing quaternary ammonium groups are disclosed in U.S. Pat. No. 3,278,465. Such materials have been found to be useful in the manufacture of certain types of polyurethane foams, e.g., those produced from polyether polyols, by the so-called "one-shot" technique disclosed in this patent. However, in the production of other types of polyurethane foams by the so-called "one-shot" technique the high molecular weight siloxanes of this patent either fail to perform adequately or fail completely. For example, in manufacuturing polyester polyurethane foams by the "one-shot" method using the high molecular weight siloxanes of this patent as stabilizers the foam collapses or is of very poor quality. Quaternary ammonium salts of siloxanes are also disclosed in U.S. Pat. No. 3,402,191 and British Pat. No. 1,164,581.

It has been found, according to the present invention, that a certain class of noval cationic siloxanes containing quaternary nitrogen as defined herein possess unique properties which render them far superior to the heretofore known siloxanes of a similar nature in such uses as the production of highly effective fire-fighting foams which are capable of forming spreading, vapor-securing films on liquid hydrocarbons such as gasoline, the production of high quality polyurethane foams by mechanical frothing techniques, or the production of high quality polyester polyurethane foams by the "one-shot" techniques.

The novel cationic siloxanes of this invention are the cationic bis(trimethylsiloxy) siloxanes having the formula:

$$MD_x'M \qquad (a)$$

wherein M is the trimethylsiloxy unit, $Me_3SiO_{\frac{1}{2}}$, $x$ is an integer of 1 to 3, preferably 1, and D' is a cationic difunctional siloxy unit of the formula:
$$X^-[R_3N^+R°(O)_tSi(Me)O] \qquad (1)$$
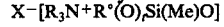

wherein R° is a divalent organic group free of aliphatic unsaturation and having 2 to 18 carbon atoms, selected from the class consisting of divalent hydrocarbon groups, hydroxy-substituted divalent hydrocarbon groups, and groups of the formula: —R"OR"— wherein R" is selected from the class consisting of divalent hydrocarbon groups and hydroxy-substituted divalent hydrocarbon groups as defined above; R is bonded to N of the formula and is selected from the class consisting of methyl and ethyl when taken individually and, when two R groups are taken together with the N atom of the above formula, a divalent group having a five to six member heterocyclic ring comprising carbon, nitrogen and hydrogen bonded through said N atom to the R° group and the remaining R group; X is an anion selected from the class consisting of iodine, bromine, chlorine, aryl sulfonate having 6 to 18 carbon atoms, nitrate, nitrite and borate anions, when taken individually; sulfate and sulfite anions when two X groups are taken together; and phosphate anion when three X groups are taken together; and $t$ is an integer of 0 to 1. Preferably X is selected from the class consisting of iodine, bromine, and aryl sulfonate having 6 to 8 carbon atoms, when taken individually, and sulfate when two X groups are taken together. More preferably, X is selected from the class consisting of iodine and bromine and most preferably is iodine. The cationic bis(trimethylsiloxy) silanes, i.e., where $x$ in the above formulas (a) and (1) is 1, are preferred.

More specifically the novel cationic siloxanes of this invention are cationic bis(trimethylsiloxy) siloxanes having the formula $MD_x'M$ wherein M is a trimethylsiloxy unit, $Me_3SiO_{\frac{1}{2}}$, $x$ is an integer of 1 to 3 and D' is a cationic difunctional unit having the formula:

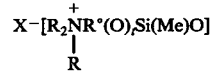

$$X^-[R_2NR°(O)_tSi(Me)O]$$

wherein R° is a divalent organic group, free of aliphatic unsaturation and having 2 to 18 carbon atoms, selected from the class consisting of divalent hydrocarbon groups and hydroxy-substituted divalent hydrocarbon groups; R is selected from the class consisting of methyl and ethyl; $R_2N$ is an organic heterocyclic radical selected from the group selected consisting of morpholinium, piperidinum, pyrrolium, and piperazinium, said heterocyclic radical being bonded through the N atom in the above formula to the R and R° groups; X is an anion selected from the class consisting of chlorine, iodine, bromine, aryl sulfonate having 6 to 18 carbon atoms, nitrate, nitrite and borate anions when taken individually, sulfate and sulfite anions when two X–groups are taken together and a phosphate anion when three X–groups are taken together; and $t L$ is an integer of 0 to 1, with the proviso that when $t$ is 1, R° can also be a group of the formula —R"OR"— wherein R" is selected from the class consisting of divalent hydrocarbon groups and hydroxy-substituted divalent hydrocarbon groups as defined above.

Typical divalent groups represented by R° in the above formulas include, ethylene, 1,3-propylene, 1,2-propylene, 1,4-butylene, 1,3-butylene, 1,5-pentylene, 1,4-pentylene and 1,6-hexylene, cycloalkylene including cyclohexylene, cyclopentylene and the like, arylene including phenylene, benzylidene, tolylene, xylylene, naphthylene, —$C_6H_4CH_2C_6H_4$—, 5,6-dimethyl-1,3-phenylene, 2,4-dimethyl-1,3-phenylene, anthrylene and the like; hydroxyl-substituted divalent hydrocarbon groups such as hydroxyalkylene groups including hydroxyethylene, 2-hydroxy-1,3-propylene, 3-hydroxy-1,2-propylene, 2-hydroxy-n-butylene, 2-hydroxy-1,3-butylene, and the like, hydroxy-cycloalkylene including 2-hydroxy-1,3-cyclopentylene, 2-hydroxy-1,4-cyclohexylene and the like, hydroxyarylene groups including 2-hydroxy-1,4-phenylene, 3-hydroxy-1,4-tolylene, 2-hydroxy-1,4-xylylene, 3-hydroxy-1,2-naphthylene, 6-hydroxy-1,2-anthrylene and the like; and divalent groups of the formula —R"OR"— wherein R" is selected from the class consisting of divalent hydrocarbon grous such as those listed above and hydroxyl-substituted divalent hydrocarbon groups such as those listed above, including by way of example, 1,3-propyleneoxy-1,3-propylene, 1,3-propyleneoxy-1,4-butylene, 1,3-propyleneoxy-1,2-butylene, 1,3-propyleneoxy-2-hydroxy-1,3-propylene, 1,2-propyleneoxy-3-hydroxy-1,4-butylene and the like.

In formula (1) typical groups having a divalent heterocyclic ring represented by two R' groups taken together with N of the formula including morpholinium,

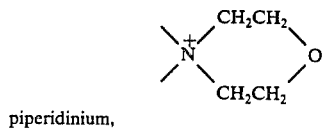

piperidinium,

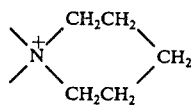

pyrrolium, piperazinium, and the like.

The organosilicon compounds containing tertiary amino groups bonded to carbon disclosed herein are the tertiary amino bis(trimethylsiloxy) siloxanes of the formula:

$$MD_xM \qquad (b)$$

wherein M and x are as defined above and D is a tertiary amino difunctional siloxy unit of the formula:

$$R_2NR°(O)_tSi(Me)O \qquad (2)$$

wherein R° and t are as defined above and R is bonded to N of formula (2) and is selected from the class consisting of methyl and ethyl, when taken individually, and, when two R groups are taken together with the N atom of formula (2), a five to six member monovalent heterocyclic ring comprising carbon, nitrogen and hydrogen bonded through said N atom to said R° group.

More specifically the novel tertiary amino bis(trimethylsiloxy) siloxanes of this invention are those having the formula MD$_x$M wherein M is the trimethylsiloxy unit Me$_3$SiO$_\frac{1}{2}$, x is an integer of 1 to 3 and D is a tertiary amino difunctional siloxy unit of the formula $$R_2NR°(O)_tSi(Me)O$$

wherein R° is a divalent organic group free of aliphatic unsaturation and having 2 to 18 carbon atoms, selected from the class consisting of divalent hydrocarbon groups and hydroxy-substituted divalent hydrocarbon groups; R$_2$N is an organic heterocyclic radical selected from the group consisting of morpholinyl, piperidyl, pyrrolyl, and piperazinyl, said heterocyclic radical being bonded through the N atom in the above formula to the R° group; and t is an integer of 0 to 1, with the proviso that when t is 1, R° can also be a group of the formula —R"OR"— wherein R" is selected from the class consisting of divalent hydrocarbon groups and hydroxy-substituted divalent hydrocarbon groups as defined above.

Typical R and R° groups for formula (2) are as listed above for formula (1). Illustrative monovalent groups having a five or six member heterocyclic ring include morpholinyl,

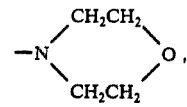

piperidyl,

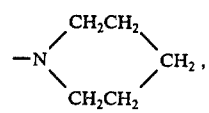

pyrrolyl, piperazinyl, and the like. The cationic bis(trimethylsiloxy) silanes, i.e., where x in formulas (b) and (2) above is 1, are preferred.

The cationic silicones of formula (1) wherein X is iodine or bromine are prepared by reacting a methyl or ethyl iodide or bromide with a tertiary amino bis(trimethylsiloxy) siloxane in accordance with the equation:

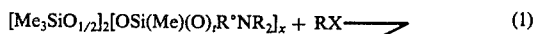

wherein R, R°, X and t are as previously defined.

Suitable halides are methyl bromide, ethyl bromide, methyl iodide, ethyl iodide and the like.

No special catalysts are needed for reaction (1). It is advantageous, however, to employ a polar solvent which dissolves both reactants and the product. Suitable solvents are the aliphatic alcohols such as n-propanol and the aliphatic ethers such as tetrahydrofuran. The amount of solvent used is not narrowly critical and can range from about 40 to about 100% of the total weight of both reactants.

Atmospheric or superatmospheric pressures can be used for reaction (1) as may be convenient for the operator. It is convenient to mix both reactants and the solvent and then maintain the resulting mixture at the reaction temperature until the reaction has been completed. However, any convenient order of mixing can be used. When a low boiling halide, such as methyl bromide, is used as a reactant, it is convenient to first mix the solvent and the siloxane and heat the resulting mixture to the reaction temperature. Then, the halide can be added in gaseous or liquid form and the reaction completed at the reaction temperature.

Reaction temperatures for reaction (1) are not narrowly critical and can be in the range of about 50° C. or less to 80° C. or more. Lower temperatures usually are impractical and high temperatures usually are unnecessary.

The cationic silicone product is conveniently separated from the reaction mixture by rotary evaporation under sub-atmospheric pressure. Any other suitable separation technique may be used. Further purification can be carried out on the separated product washing the solid product with a liquid aliphatic hydrocarbon such as pentane or hexane. Other purification techniques can be used.

Cationic silicones of formula (1) where the X groups, taken individually or two or three together, are nitrate, borate, nitrite, sulfate, sulfonate, sulfite or phosphate anions, which for convenience are called the non-halide anions, are produced by reacting the product of reaction (1), i.e., a cationic silicone of formula (1) in which X is a halide, with a soluble salt containing the non-halide anion and which forms an insoluble halide. Suitable soluble salts include silver nitrate, silver borate, silver nitrite, silver sulfate, silver aryl sulfonate, and silver sulfite. By double decomposition, the soluble salt exchanges anions with the cationic silicone halide forming the desired cationic silicone non-halide and an insoluble halide which precipitates out. For example, silver sulfate is reacted with a cationic silicone halide of the formula:

[Me$_3$SiO$_1$]$_2$[OSi(Me)(CH$_2$)$_3$N$^+$(Me)CH$_2$CH$_2$)$_2$O]I$^-$ to form the corresponding sulfate of the formula:

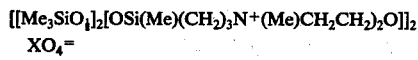
{[Me$_3$SiO$_1$]$_2$[OSi(Me)(CH$_2$)$_3$N$^+$(Me)CH$_2$CH$_2$)$_2$O]}$_2$ XO$_4$$^=$ and insoluble silver bromide which is recovered as a precipitate.

The tertiary amino bis(trimethylsiloxy) siloxane intermediates used as starting materials in reaction (1) for preparing cationic silicones having the formula (1) wherein $t=0$ are prepared by the addition reaction of the corresponding hydrosiloxane:

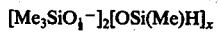
[Me$_3$SiO$_1^-$]$_2$[OSi(Me)H]$_x$ and an alkenyl group-containing tertiary organic amine in accordance with the equation:

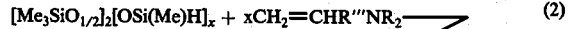
[Me$_3$SiO$_{1/2}$]$_2$[OSi(Me)H]$_x$ + xCH$_2$=CHR'''NR$_2$ ⟶ (2)

[Me$_3$SiO$_{1/2}$]$_2$[OSi(Me)R°NR$_2$]$_x$ wherein R, R° and $x$ are as defined above and wherein R''' is a divalent organic group free of aliphatic unsaturation, having 1 to 16 carbon atoms and selected from the class consisting of divalent hydrocarbon groups, hydroxy-substituted divalent hydrocarbon groups, groups of the formula —OR"— wherein R" is a divalent hydrocarbon group or hydroxy-substituted hydrocarbon group and is bonded to the N atom and wherein the oxygen is bonded to the CH$_2$=CH— group, and —R"OR— wherein R" is as defined above. It will be noted that the —R°— group comprises the group —C$_2$H$_4$R'''— which is formed when ≡SiH reacts with CH$_2$=CHR'''— in reaction (2).

The hydrosiloxanes are readily available materials and can be prepared by standard procedures. Suitable hydrosiloxanes include heptamethyltrisiloxane, octamethyltetrasiloxane, and nonamethylpentasiloxane. The alkenyl group-containing tertiary amines are also available or can be prepared by standard procedures. Illustrative amines are N-allyl-N,N-diethylamine, N-allylpiperidine, N-allylmorpholine, N-methallylmorpholine, N-allyl-N-methylaniline, N-(2-allyloxy)propylmorpholine, those listed in Table 1 below and the monoallyl or monovinyl ethers of the following amines: N,N-diethyl ethanolamine, N-N-dimethyl ethanolamine, N,N-diisopropyl ethanolamine, N,N-dimethyl propanolamine, N,N-dihexylethanolamine, N,N-dilauryl propanolamine.

In general, the reaction illustrated by equation (2) can be conducted employing, preferably, from 5 to 30 parts, per million parts by weight of the reactants, of platinum, e.g., in the form of chloroplatinic acid dissolved, if desired, in a solvent such as, tetrahydrofuran, ethanol, butanol or a mixture of ethanol and ethylene glycol dimethyl ether, or in the form of finely divided elemental platinum supported on a material such as gamma alumina or charcoal. The addition reaction is conducted at a temperature of from 60° C. to 200° C., or preferably at a temperature from about 100° C. to about 140° C. It is preferred to conduct the reaction in the presence of a liquid organic compound or solvent in which the reactants are mutually soluble. Solvents are especially preferred in reaction (2) so as to provide greater compatibility between the reactants. Suitable solvents include aromatic hydrocarbons (e.g., toluene and xylene) and ethers (e.g., ethylene glycol diethyl ether, diethylene glycol dimethyl ether, diisopropyl ether, and dipropyl ether). Such solvents can be employed in an amount from 10 parts to 1000 parts by weight per 100 parts by weight of the reactants.

The relative amounts of the alkenyl amine and the hydrosiloxane employed are not narrowly critical. Stoichiometric amounts of the reactants up to a slight excess of alkenyl amine, e.g., up to 5% excess, can be used and such slight excess of alkenyl amine can be advantageous from the standpoint of more effective and more complete reaction of silanic hydrogen.

The order in which the alkenyl amine, the hydrosiloxane and the platinum catalyst are mixed in forming a reaction mixture for use in producing the siloxanes of this invention is not critical to obtaining the desired product. The catalyst can be added separately to the alkenyl amine or to the siloxane or can be added to a mixture of these materials. It is preferable to add the catalyst to the hydrosiloxane and then add the alkenyl amine in increments since this technique aids in controlling the reactions, which are often exothermic. Additional catalyst can be added during the course of the reaction in the event the rate of reaction decreases (e.g., due to catalyst poisoning).

Thus reaction is usually completed without about 1 to about 6 hours and completeness can be readily detected by withdrawing an aliquot sample and testing with a solution of silver nitrate in an ethanol-water solvent.

The tertiary amino bis(trimethylsiloxy) siloxane intermediates used as starting materials in reaction (1) for preparing cationic silicones having the formula (1) wherein $t=1$ are prepared by the reaction of a hydrosiloxane as defined above with an organic amino alcohol in accordance with the equation:

[Me$_3$SiO$_{1/2}$]$_2$[OSi(Me)H]$_x$ + xHOR°NR$_2$ ⟶ (3)

[Me$_3$SiO$_{1/2}$]$_2$[OSi(Me)OR°NR$_2$]$_x$ wherein R, R° and $x$ are as defined above.

Suitable amino alcohols include N,N-dimethylaminoethanol, N,N-diethylaminoethanol, 1-(N,N-dimethylamino)propanol, N-[2-(2-hydroxyethoxy)ethyl]morpholine, the amino alcohols listed in Table 2 below, N,N-diisopropylethanolamine, N,N-dimethylpropanolamine, N,N-dihexylethanolamine, N,N-dilaurylpropanolamine and the like.

Reaction (3) is carried out in the presence of stannous octoate catalyst which preferably is used in amounts of about 0.05 to about 2.0% based on the total weight of the reactants, although higher or lower amounts can be used, such as in the range of about 0.1 to about 5 wt. % on the same basis. The reaction conditions specified above for the reaction of equation (2) can also be applied here.

The intermediates produced by the reaction of equations (2) and (3) can be isolated in any convenient way such as by fractional distillation under vacuum or, especially if the intermediate has a high boiling point, rotary evaporation under reduced pressure.

The cationic silicones disclosed and claimed herein are highly useful as foam stabilizers in such applications as the production of highly efficient fire-fighting foams as disclosed in U.S. Pat. No. 3,677,347, high quality polyester polyurethane foams by the "one-shot" technique as disclosed in U.S. Pat. No. 3,642,670, and high quality polyurethane foams by the mechanical frothing technique as disclosed in U.S. application Ser. No. 887,305 filed Dec. 22, 1969, now abandoned. The tertiary amino bis(trimethylsiloxy) siloxanes and the cationic silicones disclosed and claimed herein are also useful as emulsifiers for water-poly(dimethylsiloxane) systems, bacteriocides, antistatic agents, wetting agents and mold release agents.

The following examples are presented wherein all parts and percentages are by weight and all temperatures are on the Centigrade scale. Boiling points, evaporation conditions and distillation conditions are given in degrees Centigrade at a pressure given in millimeters of mercury, e.g., 63°/1 mm which means 63° C. at 1 mm Hg pressure. Washing conditions are expressed in the number of washes and the amount of washing liquid for each wash, e.g., 6 × 100 ml which means washed six times using 100 ml washing liquid each time. Also, the designation

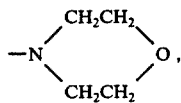

the designation —NC$_5$H$_{10}$ represents the piperidinyl group

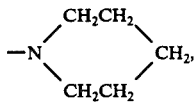

the designation >N+(CH$_2$CH$_2$)$_2$O represents the morpholinium group

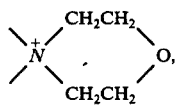

and the designation >N+C$_5$H$_{10}$ represents the piperidinium group

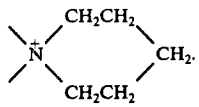

EXAMPLE 1

Preparation of [Me$_3$SiO)$_2$MeSi(CH$_2$)$_3$N+Me$_3$]I$^-$

A. To a 500 ml. flask equipped with thermometer, stirrer, dropping funnel and nitrogen atmosphere were added heptamethyltrisiloxane (132.2 g., 0.594 mole) and 100 ml. of toluene. The reaction mixture was heated to 80° and then 10 parts per million platinum was added as chloroplatinic acid. To this mixture, N-allyl-N,N-dimethylamine (50.5 g., 0.594 mole) was added dropwise while maintaining the reaction mixture at 80°—90°. After the completion of addition, the reaction mixture was kept at 80°-90° for 1 hr. The mixture was then cooled and neutralized by NaCHO$_3$, filtered and fractionally distilled. There was obtained 162.0 g (88.7%) of the intermediate, (Me$_3$SiO)$_2$MeSi(CH$_2$)$_3$NMe$_2$, which had a boiling point of 63°/1 mm.

Anal. Calc. for C$_{12}$H$_{33}$NO$_2$SI$_3$: C, 46.9H, 10.7; N, 4.6; Si, 27.4.

Found: C, 46.3; H, 10.2; N, 3.8; Si, 26.4%.

B. 60.0 g (0.195 mole) of this intermediate was dissolved in 50 ml. of tetrahydrofuran. To this mixture, 55.4 g. (0.390 mole) of methyl iodide were added slowly at room temperature with constant stirring. The reaction mixture was stirred at 25° for 1 hour. Removal of solvent by rotary evaporation afforded a white solid which was mixed with hexane (100 ml.) and filtered to give 42.8 g. (81.7%) of the intermediate.

Anal. Calc. for C$_{13}$H$_{36}$INO$_2$Si$_3$: C, 34.7; H, 8.0; I, 28.2; N, 3.1; Si, 18.8.

Found: C, 34.9; H, 8.2; I, 27.4; N, 3.0; Si, 18.9%.

The product when dissolved in tap water at a concentration of 1 wt. % and whipped, produced a fire-fighting foam that formed a long-loasting, spreading, vapor-securing film on gasoline. When mixed with a polyester-containing, blowing agent-containing, polyurethane-forming composition on the basis of 1 wt. pt. per hundred wt. pts. of polyester, a high quality, breathable foam was obtained.

EXAMPLE 2

Preparation of [(Me$_3$SiO)$_2$MeSi(CH$_2$($_3$N'Me$_3$]Cl$^-$

The amino-modified siloxane was prepared as described in Example 1, Section A. 102.5 g. (0.33 mole) of this compound were dissolved in 200 ml. of tetrahydrofuran in a flask equipped with stirrer, dry ice condenser, thermometer and gas dispersion tube. The solution was heated to 60°. Then gaseous methyl chloride (40 g., 0.8 mole) was passed into it over a period of 2 hours. After the completion of addition, the reaction mixture was maintained at 50°-60° for 2 more hours. Rotary evaporation of all matter volatile at 30°/1 mm. afforded a white waxy solid which was purified by washing with hexane (6 × 100 ml.) which resulted in a microcrystalline white powder product in 60% yield.

Anal. Calc. for C$_{13}$H$_{36}$ClNO$_2$Si$_3$: C, 43.6; H, 10.1; Cl, 9.9; N, 3.9; Si, 23.5. Found: C, 41.4; H, 10,0; Cl, 8.8; N, 3.5; Si, 22.1%.

The product when dissolved in tap water at a concentration of 1 wt. %, produced a fire-fighting foam that provided a long-lasting, spreading, vapor-securing film on gasoline.

EXAMPLE 3

Preparation of [(Me$_3$SiO)$_2$MeSi(CH$_2$)$_3$N+Me$_3$]Br−

The amino-modified siloxane was prepared as described in Example 1, Section A. 102.5 g. (0.33 mole) of this compound were dissolved in 150 ml. dry tetrahydrofuran. The solution was charged to a three-necked 500 ml. flask equipped with a dry ice condenser, heating mantle, stirrer and thermometer. Methyl bromide was slowly bubbled in (47.5 g., 0.5 mole). This caused an exotherm to 45°. After the completion of addition, the mixture was heated to reflux (66° ) and kept at that temperature for four hours. The mixture was then cooled and solvent was removed by rotary evaporation. The white solid residue was mixed with 200 ml. of hexane and filtered to give 86.0 g. (65%) of the product.

Anal. Calc. for C$_{13}$H$_{36}$BrNO$_2$Si$_3$: C, 38.7; H, 8.9; Br, 19.8; N, 3.4; Si, 20.9. Found: Br, 18.9; Si, 20.1%.

The product when dissolved in tap water at a concentration of 1 wt. %, produced a fire-fighting foam that provided a long-lasting, spreading, vapor-securing film on gasoline.

EXAMPLE 4

Preparation of [(Me$_3$SiO)$_2$MeSi(CH$_2$)$_3$(Me)N+C$_5$H$_{10}$]I−

A. N-allylpiperidine (62.6 g., 0.5 mole) was added to heptamethyltrisiloxane (111.2 g., 0.5 mole) almost at once. The apparatus comprised a three-necked flask, fitted with thermometer, condenser and stirrer. The reaction was carried out under nitrogen atmosphere. 200 ml. of dry xylene were used as solvent. To this mixture 15 parts per million of platinum as chloroplatinic acid were added and then refluxed at 138° until all of the SiH had been consumed as evidenced by the silver nitrate test. After the completion of the reaction (1 hour), the mixture was cooled and neutralized by NaHCO$_3$, filtered and all matter volatile at 30°/1 mm. was removed by rotary evaporation. The residue was fractionally distilled at 98°/0.2 mm. to give the desired intermediate, (Me$_3$SiO)$_2$MeSi(CH$_2$)$_3$NC$_5$H$_{10}$, (148.2 g.) in 85.4% yield.

Anal. Calc. for C$_{15}$H$_{37}$NO$_2$Si$_3$: C, 51.8; H, 10.7; N, 4.0; Si, 24.2. Found: C, 49.4; H, 10.0; N, 3.9; Si, 24.3%.

B. 69.53 g. (0.2 mole) of the above intermediate were reacted with methyl iodide (33.06 g., 0.232 mole) in a 500 ml. round bottom flask without solvent. The mixing of the two reagents was carried out with vigorous stirring. There was an exothermal reaction noted and soon after the addition was complete, a white precipitate formation was apparent. After about 10 minutes the reaction mixture solidified. To this mixture, 250 ml. of pentane were added, mixed well and filtered. The precipitate was washed with 2 × 70 ml. of pentane to give 85.0 g., 87% of the product.

Anal. Calc. for C$_{16}$H$_{40}$INO$_2$Si$_3$: C, 39.3; H, 8.2; I, 25.9; N, 2.9; Si, 17.2. Found: C, 40.1; H, 8.3; I, 22.5; N, 3.0; Si, 18.0%.

The product when dissolved in tap water at a concentration of 1 wt. %, produced a fire-fighting foam that provided a long-lasting, spreading, vapor-securing film on gasoline.

When mixed with a polyester-containing, polyurethane-forming composition, on the basis of 1 wt. pt. per hundred wt. pts. of polyester, there was produced a high quality foam.

EXAMPLE 5

Preparation of [(Me$_3$SiO)$_2$MeSi(CH$_2$)$_3$(Me)N+(CH$_2$CH$_2$)$_2$O]I−

A. N-allylmorpholine (100.0 g., 0.787 mole) was added to heptamethyltrisiloxane (175.0 g., 0.787 mole) almost at once. The apparatus comprised a three-necked flask, fitted with thermometer, condenser and stirrer. The reaction was carried out under nitrogen atmosphere. Toluene (200 ml.) was used as solvent. To this mixture 10 parts per million of platinum were added as chloroplatinic acid. The reaction mixture was then refluxed (110° ) for 3 hours. After the completion of the reaction, the mixture was cooled, neutralized by NaHCO$_3$ and filtered. Removal of the volatiles at 30°/1 mm. by rotary evaporation afforded a straw colored resdue, (Me$_3$SiO)$_2$MeSi(CH$_2$)$_3$N(CH$_2$CH$_2$)O, 261.7 g. in 95.2% yield.

Anal. Calc. for C$_{14}$H$_{35}$NO$_3$Si$_3$: C, 48.1; H, 10.0; N, 4.0; Si, 24.1.

Found: C, 47.6; H, 10.3; N, 3.8; Si, 22.2%.

B. 100 g. (0.286 mole) of the above prepared siloxane were dissolved in 100 ml. tetrahydrofuran. To this mixture 60.9 g. (0.429 mole) of methyl iodide were added and the mixture was stirred at 25° for 16 hours. Removal of the solvent by rotary evaporation afforded a white solid which was washed with 200 ml. of pentane and filtered. There was obtained 136.9 g. (97.8%) of the product.

Anal. Calc. for C$_{15}$H$_{38}$IO$_3$Si$_3$: C, 36.6; H, 7.7; I, 25.8; N, 2.9; Si, 17.1. Found: C, 36.7; H, 8.8; I, 25.4; N, 2.8; Si, 17.0%.

When mixed with a polyurethane forming composition and mechanically frothed with air, a stable, curable froth having a density of 16 pounds per cubic foot or less was obtained.

EXAMPLE 6

Preparation of [(Me$_3$SiO)$_2$MeSi(CH$_2$)$_3$(Me)$_2$N+C$_6$H$_5$]I−

A. N-allyl-N-methylaniline (50.0 g., 0.339 mole) was added to heptamethyltrisiloxane (75.5 g., 0.339 mole) dissolved in 100 ml. of xylene. To this mixture 15 parts per million of platnium were added as chloroplatinic acid. The reaction mixture was heated at 120-135° for 1 hour. After this time all of the SiH had been consumed as evidenced by the silver nitrate test. After cooling, the mixture was neutralized by NaHCO$_3$ and filtered. Removal of solvent by rotary evaporation at 30°/1 mm. afforded the intermediate (Me$_3$SiO)$_2$MeSi(CH$_2$)$_3$—(-Me)NC$_6$H$_5$, in 89% yield (111.0 g.).

Anal. Calc. for C$_{17}$H$_{35}$NO$_2$Si$_3$: C, 55.2; H, 9.5; N, 3.8 Si, 22.8. Found: C, 58.4; H, 9.5; N, 4.2; Si, 20.3%.

B. 20.0 g. (0.054 mole) of the above prepared siloxane were reacted with methyl iodide (10.5 g., 0.073 mole) in 30 ml. of benzene for 25 hours at 25°. After removal of the solvent by rotary evaporation at 30°/1 mm., the resultant solid was mixed with pentane (150 ml.) and filtered. There was obtained 25.0 g. (90.25%) of the product as a white crystalline solid.

Anal. Calc. for C$_{18}$H$_{38}$INO$_2$Si$_3$: C, 42.2; H, 7.5; I, 24.8; N, 2.7; Si, 16.5.

Found: C, 44.7; H, 7.2; I, 22.7; N, 2.7; Si, 15.1%.

When mixed with a polyester-containing, polyruethane-forming composition, on the basis of 1 wt. pt. per hundred wt. pts. of polyester, there was produced a high quality foam.

EXAMPLE 7

Preparation of
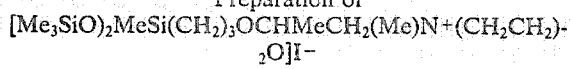

A. Heptamethyltrisiloxane (111.2 g., 0.5 mole) and 150 ml. of toluene were placed in a 500 ml. flask equipped with condenser, stirrer, thermometer and dropping funnel. The solution was heated to 100° and 20 parts per million platinum were added as chloroplatinic acid. To this mixture, N-(2-allyloxy) propylmorpholine (93.5 g., 0.5 mole) was added slowly over a period of 15 minutes, and then the mixture was maintained at reflux temperature (110°) for 2 hours. After cooling, the mixture was neutralized by $NaHCO_3$ and filtered. The intermediate, $(Me_3SiO)_2$—$MeSi(CH_2)_3OCH$-$MeCH_2N(CH_2CH_2)_2O$, was isolated by fractional distillation at 114°/0.14 mm. The yield was 163.8 g. (80%).

Anal. Calc. for $C_{17}H_{41}NO_4Si_3$: C, 50.1; H, 10.1; N, 3.4; Si, 20.6. Found: C, 47.4; H, 9.7; N, 3.3; Si, 20.5%.

B. This intermediate (80.0 g., 0.195 mole) and methyl iodide (55.5 g., 0.39 mole) and 100 g. of tetrahydrofuran were mixed in a 500 ml. flask equipped with stirrer and condenser. The reaction mixture was maintained at reflux for 3 hours. After this time the reaction mixture was cooled and the solvent was removed by rotary evaporation at 30°/1 mm. to give 102 g. (94.7%) of the product.

Anal. Calc. for $C_{18}H_{44}INO_4Si_3$: C, 39.3; H, 8.0; I, 23.1; N, 2.6; Si, 15.3.

Found: C, 38.2; H, 7.6; I, 23.1; N, 2.5; Si, 15.3%.

The product when dissolved in tap water at a concentration of 1 wt. %, produced a fire-fighting foam that provided a long-lasting, spreading, vapor-securing film on gasoline.

When mixed with a polyester-containing, polyurethane-forming composition, on the basis of 1 wt. pt. per hundred wt. pts. of polyester, there was produced a high quality foam.

When mixed with a polyurethane-forming composition and mechanically frothed with air, a stable, curable froth having a density of 16 pounds per cubic foot or less was obtained.

EXAMPLE 8

(Preparation of
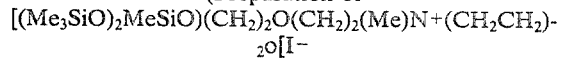

A. N-[2-(2-hydroxyethoxy) ethyl] morpholine (43.7 g., 0.25 mole) and heptamethyltrisiloxane (55.5 g., 0.25 mole) were reacted together in the presence of 0.2 wt. % stannous octoate catalyst. The apparatus comprised a three-necked flask, fitted with thermometer, condenser and stirrer. The reaction was carried out under nitrogen atmosphere. The reaction mixture was heated at 110°-120° with constant stirring for 4 hours. Evolution of hydrogen was noted soon after heating started. The completion of the reaction was evidenced by the negative silver nitrate test for SiH. The intermediate, $(Me_3SiO)_2MeSiO(CH_2)_2)(CH_2)N(CH_2CH_2)_2O$, was obtained in 100% yield.

Anal. Calc. for $C_{15}H_{37}NO_5Si_3$: C, 45.5; H, 9.4; N, 3.5; Si, 21.3.

Found: C, 42.0; H, 9.2; N, 2.9; Si, 27.6%.

B. This intermediate (36.5g., 0.092 mole) and methyl iodide (19.6 g., 0.138 mole) were mixed together in the presence of 100 ml. of tetrahydrofuran. The reaction mixture was allowed to stir for 16 hours. at 25°. Removal of solvent by rotary evaporation afforded a slightly colored solid product (40.5 g.) in 82.5% yield.

Anal. Calc. for $C_{16}H_{40}INO_5Si_3$: C, 35.7; H, 7.4; I, 23.6; N, 2.6; Si, 15.6. Found: C, 33.3; H, 7.3; I, 19.7; N, 2.2; Si, 21.7%.

The product when dissolved in tap water at a concentration of 1 wt. %, produced a fire-fighting foam that provided a long-lasting, spreading, vapor-securing film on gasoline.

When mixed with a polyurethane-forming composition and mechanically frothed with air, a stable, curable froth having a density of 16 pounds per cubic foot or less was obtained.

Using the procedure of Example 1, Section A, heptamethylsiloxane is reacted with the allylic amines listed in Table 1 to produce the tertiary aminohydrocarbyl bis(trihydrocarbylsiloxy) silanes also listed in Table 1.

TABLE 1

| Amine | Product |
|---|---|
| $CH_2=CHCH_2NEt_2$ | $(Me_3SiO)_2MeSi(CH_2)_3NEt_2$ |
| $CH_2=CHCHMeN(CH_2CH_2)_2O$ | $(Me_3SiO)_2MeSiCH_2CH_2CH$-$MeN(CH_2CH_2)_2O$ |
| $CH_2=CHCH_2OCH_2CH(OH)CH_2$-$N(CH_2CH_2)_2O$ | $[Me_3SiO]_2MeSi(CH_2)_3OCH_2$-$CH(OH)CH_2N(CH_2CH_2)_2O$ |

Using the procedure of Example 8, Section A, heptamethylsiloxane was reacted with the hydroxyamines listed in Table 2 to produce the tertiary aminohydroxarbyloxy bis(trihydrocarbylsiloxy) silanes also listed in Table 2.

TABLE 2

| Amine | Product |
|---|---|
| $HOCHMeCH_2NMe_2$ | $(Me_3SiO)_2MeSiOCHMeCH_2NMe_2$ |
| $HOCH_2CH_2NMe_2$ | $(Me_3SiO)_2MeSiOCH_2CH_2NMe_2$ |
| $HOCH_2CH_2NEt_2$ | $(Me_3SiO)_2MeSiOCH_2CH_2NEt_2$ |
| $HOCHMeCH_2NEt_2$ | $(Me_3SiO)_2MeSiOCHMeCH_2NEt_2$ |
| $HOCH(Me)CH_2$-$N(CH_2CH_2)_2O$ | $(Me_3SiO)_2MeSiOCH(Me)CH_2N(CH_2$-$CH_2)_2O$ |

Using the procedure of Section B of Examples 1 or 4 through 8 or the procedure of Examples 2 or 3, corresponding to the alkyl halide used, the siloxanes listed in Table 3 were reacted with the alkyl halides listed in Table 3 to produce the products listed in Table 3.

TABLE 3

| Siloxane | Alkyl Halide | Product |
|---|---|---|
| $(Me_3SiO)_2MeSi(CH_2)_3NMe_2$ | EtI | $[(Me_3SiO)_2MeSi(CH_2)_3N^+Me_2Et]I^-$ |
| $(Me_3SiO)_2MeSi(CH_2)_3NEt_2$ | MeI | $[(Me_3SiO)_2MeSi(CH_2)_3N^+Et_2Me]I^-$ (a,b) |
|  | EtI | $[(Me_3SiO)_2MeSi(CH_2)_3N^+Et_3]I^-$ (a,b) |
|  | MeBr | $[(Me_3SiO)_2MeSi(CH_2)_3N^+Et_2Me]Br^-$ |
| $(Me_3SiO)_2MeSi(CH_2)_2CHMeN(CH_2CH_2)_2O$ | MeI | $[(Me_3SiO)_2MeSi(CH_2)_2CHMe(Me)N^+(CH_2CH_2)_2O]I^-$ (c) |
| $(Me_3SiO)_2MeSi(CH_2)_3N(CH_2CH_2)_2O$ | MeBr | $[(Me_3SiO)_2MeSi(CH_2)_3(Me)N^+(CH_2CH_2)_2O]Br^-$ (a) |
| $(Me_3SiO)_2MeSi(CH_2)_3NC_5H_{10}$ | EtI | $[(Me_3SiO)_2MeSi(CH_2)_3(Et)N^+C_5H_{10}]I^-$ |
| $(Me_3SiO)_2MeSiOCHMeCH_2NMe_2$ | MeI | $[(Me_3SiO)_2MeSiOCHMeCH_2N^+Me_3]I^-$ (a,c) |
|  | EtI | $[(Me_3SiO)_2MeSiOCHMeCH_2N^+Me_2Et]I^-$ |
| $(Me_3SiO)_2MeSiO(CH_2)_2NMe_2$ | MeI | $[(Me_3SiO)_2MeSiO(CH_2)_2N^+Me_3]I^-$ |
| $(Me_3SiO)_2MeSiO(CH_2)_2NEt_2$ | MeI | $[(Me_3SiO)_2MeSiO(CH_2)_2N^+Et_2Me]I^-$ |
|  | EtI | $[(Me_3SiO)_2MeSiO(CH_2)_2N^+Et_3]I^-$ |

TABLE 3-continued

| Siloxane | Alkyl Halide | Product |
|---|---|---|
| (Me₃SiO)₂MeSiOCHMeCH₂NEt₂ | MeI | [(Me₃SiO)₂MeSiOCHMeCH₂N⁺Et₂Me]I⁻ |
| (Me₃SiO)₂MeSiOCH(Me)CH₂N(CH₂CH₂)₂O | MeI | [(Me₃SiO)₂MeSiOCH(Me)CH₂(Me)N⁺(CH₂CH₂)₂O]I⁻ (c) |
| (Me₃SiO)₂MeSi(CH₂)₃OCH₂CH(OH)CH₂N(CH₂CH₂)₂O | MeI | [(Me₃SiO)₂MeSi(CH₂)₃OCH₂CH(OH)CH₂(Me)N⁺(CH₂CH₂)₂O]I⁻ (b,c) |

(a)The product when dissolved in tap water at a concentration of 1 wt. %, produced a fire-fighting foam that provided a long-lasting, spreading, vapor-securing film on gasoline.

(b)When mixed with a polyester-containing, polyurethane-forming composition, on the basis of 1 wt. pt. per hundred wt. pts. of polyester, there was produced a high quality foam.

(c)When mixed with a polyurethane-forming composition and mechanically frothed with air, a stable, curable froth having a density of 16 pounds per cubic foot or less was obtained.

What is claimed is:

1. A cationic bis(trimethylsiloxy) siloxane having the formula MD$_x$'M wherein M is a trimethylsiloxy unit, Me₃SiO$_{\frac{1}{2}}$, x is an integer of 1 to 3 and D' is a cationic difunctional unit having the formula:

$$X^{-}[R_2\overset{+}{N}R°(O)_{\frac{1}{2}}Si(Me)O]$$
$$\underset{R}{|}$$

wherein R° is a divalent organic group, free of aliphatic unsaturation and having 2 to 18 carbon atoms, selected from the class consisting of divalent hydrocarbon groups and hydroxy-substituted divalent hydrocarbon groups; R is selected from the class consisting of methyl and ethyl; R₂N is an organic heterocyclic radical selected from the group consisting of morpholinium, piperidinum, pyrrolium, and piperazinium, said heterocyclic radical being bonded through the N atom in the above formula to the R and R° groups; X is an anion selected from the class consisting of chlorine, iodine, bromine, aryl sulfonate having 6 to 18 carbon atoms, nitrate, nitrite and borate anions when taken individually, sulfate and sulfite anions when two X⁻ groups are taken together and a phosphate anion when three X⁻ groups are taken together; and t is an integer of 0 to 1, with the proviso that when t is 1, R° can also be a group of the formula —R″OR″— wherein R″ is selected from the class consisting of divalent hydrocarbon groups and hydroxy-substituted divalent hydrocarbon groups as defined above.

2. A cationic bis(trimethylsiloxy)siloxane as defined in claim 1, wherein X⁻ is an anion selected from the class consisting of chlorine, iodine, bromine and aryl sulfonate having 6 to 18 carbon atoms.

3. A cationic bis(trimethylsiloxy) siloxane, as defined in claim 2, wherein R° is selected from the class consisting of alkylene and hydroxy-substituted alkylene when t is 0 and also groups of the formula —R″OR″— wherein R″ is selected from the class consisting of alkylene and hydroxy-substituted alkylene as defined above when t is 1.

4. A cationic bis(timethylsiloxy) siloane as defined in claim 3, wherein R₂N is morpholinium or piperidinum.

5. A cationic bis(trimethylsiloxy) siloxane as defined in claim 4, wherein R₂N is morpholinium and t is 1.

6. A cationic bis(trimethylsiloxy) siloxane as defined in claim 4, wherein R₂N is morpholinium and t is 0.

7. A siloxane as defined in claim 1, having the formula

[(Me₃SiO)₂MeSi(CH₂)₃OCHMeCH₂(Me)N⁺(CH₂CH₂)₂O]I⁻

8. A siloxane as defined in claim 1, having the formula

[(Me₃SiO)₂MeSiO(CH₂)₂O(CH₂)₂(Me)N⁺(CH₂CH₂)₂O]I⁻

9. A siloxane as defined in claim 1, having the formula

[(Me₃SiO)₂MeSi(CH₂)₃(Me)N⁺(CH₂CH₂)₂O]I⁻

10. A siloxane as defined in claim 1, having the formula

[(Me₃SiO)₂MeSi(CH₂)₃OCH₂CH(OH)CH₂(Me)N⁺(CH₂CH₂)₂O]I⁻

11. A siloxane as defined in claim 1, having the formula

[(Me₃SiO)₂MeSiOCHMeCH₂(Me)N⁺(CH₂CH₂)₂O]I⁻

12. A siloxane as defined in claim 1, having the formula

[(Me₃SiO)₂MeSi(CH₂)₂CHMe(Me)N⁺(CH₂CH₂)₂O]I⁻

13. A siloxane as defined in claim 1, having the formula

[(Me₃SiO)₂MeSi(CH₂)₃(Me)N⁺(CH₂CH₂)₂O]Br⁻

14. A siloxane as defined in claim 1, having the formula

[(Me₃SiO)₂MeSi(CH₂)₃(Me)N⁺(CH₂CH₂)₂O]SO₄³²

15. A tertiary amino bis(trimethylsiloxy) siloxane having the formula MD$_x$M wherein M is the trimethylsiloxy unit Me₃SiO$_{\frac{1}{2}}$, x is an integer of 1 to 3 and D is atertiary amino difunctional siloxy unit of the formula R₂NR°(O)$_{\frac{1}{2}}$Si(Me)O wherein R° is a divalent organic group free of aliphatic unsaturation and having 2 to 18 carbon atoms, selected from the class consisting of divalent hydrocarbon groups and hydroxy-subtituted divalent hydrocarbon groups; R₂N is an organic heterocyclic radical selected from the group consisting of morpholinyl, piperidyl, pyrrolyl, and piperazinyl, said heterocyic radical being bonded through the N atom in the above formula to the R° group; and t is an integer of 0 to 1, with the proviso that when t is 1, R° can also be group of the formula —R″OR″— wherein R″ is selected from the class consisting of divalent hydrocarbon groups and hydroxy-substituted divalent hydrocarbon groups as defined above.

16. A tertiary amino bis(trimethylsiloxy) siloxane defined in claim 15, wherein R° is selected from the class consisting of alkylene and hydroxy-substituted alkylene when t is 0 and also groups of the formula —R″OR″— wherein R″ is selected from the group consisting of alkylene and hydroxy-substituted alkylene as defined above when t is 1.

17. A tertiary amino bis(trimethylsiloxy) siloxane as defined in claim 16, wherein R₂N is morpholinyl or piperidyl.

18. A tertiary amino (trimethylsiloxy) siloxane as defined in claim 17, wherein $R_2N$ is morpholinyl and $t$ is 1.

19. A tertiary amino (trimethylsiloxy) siloxane as defined in claim 17, wherein $R_2N$ is morpholinyl and $t$ is 0.

20. A siloxane as claimed in claim 1 having the formula:

$$[(Me_3SiO)_2MeSi(CH_2)_3(Me)N^+C_5H_{10}]I^-.$$

* * * * *